United States Patent
Jung et al.

(10) Patent No.: US 12,037,373 B2
(45) Date of Patent: Jul. 16, 2024

(54) MULTIMERIC AND MULTIVALENT POLYMER COMPRISING MULTIMERIZATION PEPTIDE DOMAIN

(71) Applicant: EarwynTech, Gyeongsangnam-do (KR)

(72) Inventors: Tae Sung Jung, Gyeongsangnam-do (KR); Jung Seok Lee, Busan (KR); Se Pyeong Im, Daegu (KR); Jaesung Kim, Gyeongsangnam-do (KR); Young Rim Kim, Gyeongsangnam-do (KR)

(73) Assignee: EarwynTech, Gyeongsangnam-Do (KR)

( * ) Notice: Subject to any disclaimer, the term of this patent is extended or adjusted under 35 U.S.C. 154(b) by 1064 days.

(21) Appl. No.: 16/456,204

(22) Filed: Jun. 28, 2019

(65) Prior Publication Data

US 2019/0315817 A1 Oct. 17, 2019

Related U.S. Application Data

(63) Continuation-in-part of application No. PCT/KR2017/003937, filed on Apr. 12, 2017.

(30) Foreign Application Priority Data

Dec. 30, 2016 (KR) .................... 10-2016-0183813

(51) Int. Cl.
  *C07K 14/46* (2006.01)
  *G01N 33/543* (2006.01)
(52) U.S. Cl.
  CPC ..... *C07K 14/461* (2013.01); *G01N 33/54346* (2013.01); *C07K 2319/00* (2013.01); *C07K 2319/30* (2013.01)
(58) Field of Classification Search
  CPC ............... A61K 2300/00; A61K 31/19; A61K 31/7004; A61K 33/06; A61K 33/14; A61K 33/26; A61K 47/02; A61K 9/08; A61K 9/5036; A61M 1/1654; A61M 1/287
  See application file for complete search history.

(56) References Cited

U.S. PATENT DOCUMENTS

| 2007/0160628 A1* | 7/2007 | Birkett | ................... C12N 7/00 435/6.16 |
| 2011/0165584 A1 | 7/2011 | Pancer et al. | |
| 2014/0088292 A1 | 3/2014 | Kim et al. | |

FOREIGN PATENT DOCUMENTS

| KR | 10-1220162 B1 | 1/2013 | |
| KR | 10-1587386 B1 | 11/2015 | |
| WO | WO-9723631 A2 * | 7/1997 | ........... C07K 14/005 |
| WO | WO-2004071493 A1 * | 8/2004 | ........... A61K 9/5169 |
| WO | WO 2014/020069 A1 | 2/2014 | |
| WO | WO-2017066484 A2 * | 4/2017 | ............. A61K 39/12 |

OTHER PUBLICATIONS

Sean W. Phippen, Multivalent Display of Antifreeze Proteins by Fusion to SelfAssembling Protein Cages Enhances Ice-Binding Activities, Biochemistry 2016, 55, 6811-6820.*
Xuanzi Fan, Dimerization of p15RS mediated by a leucine zipper-like motif is critical for its inhibitory role on Wnt signaling, J. Biol. Chem. (2018) 293(20) 7618-7628.*
Uniprot protein Database (P03069, GCN4, accessed on Aug. 10, 2023).*
Nooraei, Virus-like particles: preparation, immunogenicity and their roles as nanovaccines and drug nanocarriers J Nanobiotechnol (2021) 19:59, pp. 1-27).*
International Search Report for PCT/KR2017/003937 mailed on Nov. 29, 2017.
Flajnik et al, "Orgin and Evolution of the Adaptive Immune System: Genetic Events and Selective Pressures", Nature Reviews Genetics, vol. 11, pp. 47-59, 2010.
Pancer et al., "Variable Lymphocyte Receptors in Hagfish", PNAS, vol. 102, No. 26. pp. 9224-9229, 2005.
Kim et al. "Multimerized Variable Lymphocyte Receptors B of Hagfish Induced by Hydrophobic Clustering", International Symposium of Korean Society of Veterinary Science, vol. 56, No. 3, p. 47, 2016.
Kim et aL "Globular-shaped Variable Lymphocyte Receptors (VLRs) of Hagfish: a Primordial Antibody in Vertebrates", in Antibody Engineering & Therapeutics, 11-15, 2016.

* cited by examiner

*Primary Examiner* — Julie Ha
*Assistant Examiner* — Erinne R Dabkowski
(74) *Attorney, Agent, or Firm* — The PL Law Group, PLLC

(57) ABSTRACT

A multivalent polymer includes a multimerization peptide domain and a target protein fused directly or indirectly with the multimerization peptide domain. The multivalent polymer exhibits a probe effect by establishing a nano-size by self-assembly, and, accordingly, the multivalent polymer can be advantageously used in the development of a highly sensitive protein nano chip and the development of a diagnostic kit.

5 Claims, 9 Drawing Sheets
Specification includes a Sequence Listing.

MULTIMERIC AND MULTIVALENT POLYMER COMPRISING MULTIMERIZATION PEPTIDE DOMAIN

CROSS REFERENCE TO RELATED APPLICATIONS

The present application is a continuation in part application to International Application No. PCT/KR2017/003937 with an International Filing Date of Apr. 12, 2017, which claims the benefit of Korean Patent Application No. 10-2016-0183813, filed in the Korean Intellectual Property Office on Dec. 30, 2016, the entire contents of which are incorporated herein by reference.

TECHNICAL FIELD

The present invention relates to a multimeric and multivalent polymer including a multimerization peptide domain.

BACKGROUND ART

With regard to protein detection techniques that are based on specific protein-protein interaction, for example, an interaction between an antigen and an antibody, it is important to have the activation of a protein probe and maintaining the specific binding property to a target substance. Conventional methods involving adhesion of a protein on a surface of various kinds of a solid substrate of a protein chip are mostly related to immobilization which is based on simple adsorption/diffusion or covalent binding of primary amine groups of a protein, or a method based on the immobilization. However, proteins are generally adhered on a substrate surface in a random manner and structures of the proteins are easily deformed to cause a lower protein activity, and thus there is a serious problem that inefficient specific binding is yielded as the binding to a surface material becomes impossible. Furthermore, in a case in which a protein probe is immobilized on a substrate surface by simple adsorption, there is also a problem that the protein probe may be washed out at intensive washing conditions during a detection process or transferred to other molecule on a substrate surface having higher affinity, and, most of all, it is difficult to quantitatively control the protein probe to get immobilized on a surface of a protein chip substrate and maintain the probe in active state.

Unlike the organic or inorganic nano particles of a related art that are artificially synthesized (e.g., metal nano particles), protein nano particles are synthesized by self-assembly in cells of a living organism, and they not only have a homogeneous particle size distribution and stability but also can be produced easily and economically in large amounts in cells of a microorganism. Furthermore, through a surface modification based on genetic engineering techniques, they can be developed into protein nano particles having various properties/functions, and they also have advantages that, when exposed to a peptide or a protein for detection (i.e., probe for detecting a disease marker) on a surface in particular, constant orientation, high directness, and structural stability can be achieved so that they are used as a material of a probe for diagnosis system having high sensitivity.

However, the techniques for producing a three-dimensional protein nano structure which have been reported in a related art have a problem that they are not suitable for a protein in terms of the production conditions like an acidic pH condition or high production temperature, and also a special chemical treatment is necessary for a material to be built up and the process time is relatively long.

Meanwhile, VLR (variable lymphocyte receptor) identified from lampreys and hagfishes, which are the lowest jawless vertebrates (Agnatha), is a polypeptide resulting from somatic rearrangement of 1 to 12 LRR (leucine-rich repeat) modules and it exhibits adaptive immunity like an antibody. Compared to an antigen receptor derived from jawed vertebrates (Gnathostomata) which is formed of a multi-domain conjugate having large molecular weight (e.g., about 150 kDa for immunoglobulin), VLR is a single polypeptide with smaller size, and also, as a single antigen receptor not employing any immunoglobulin structure that has been found until now, it can be used as a substitute of conventional antibodies.

Following the identification and separation, in order to use VLR as a substitute of conventional antibodies, a method of producing easily and quickly a large amount of a VLR protein binding to a specific antigen is being developed in recent years.

In Korean Patent Application Publication No. 2015-0037959, "Method for producing monomeric and multimeric molecules and uses thereof" is disclosed, and, in Korean Patent Registration No. 1587386, "Recombinant fluorescent protein nano particles for in vivo imaging" is disclosed. However, the multimeric and multivalent polymer including a multimerization peptide domain of the present invention has not been disclosed.

SUMMARY

Embodiments of the present invention is devised under the circumstances described above, and the inventors of the present invention found that monomers of hagfish VLRB protein aggregate to each other to form a multimer with a size of about 1,700 to 650 kDa, and the inventors recognized that this phenomenon is based on formation of a core by the hydrophobic tail (hydrophobic clustering, HC) at the carboxy terminal of VLRB protein to yield an antibody with globular-shaped multimer structure. It was further found that, as a result of substituting the hydrophobic tail at carboxy terminal of VLRB protein with a peptide domain which forms a dimer, a trimer, a tetramer, a pentamer, a hexamer, a heptamer, an octamer, or a decamer, various forms of a VLRB multimer are generated, and thus the present invention is completed accordingly.

To solve the problems that are described in the above, an embodiment of the present invention provides a multivalent polymer including a multimerization peptide domain and a target protein to form nano particles of a multimer by self-assembly of a monomer.

An embodiment of the present invention further provides a nucleic acid encoding the aforementioned multivalent polymer.

An embodiment of the present invention further provides a recombinant expression vector including the aforementioned nucleic acid.

An embodiment of the present invention further provides a host cell transformed with the aforementioned recombinant expression vector.

An embodiment of the present invention further provides a method for producing a multivalent polymer forming nano particles, including obtaining a polyvalent polymer forming nano particles from host cells transformed with the aforementioned recombinant expression vector.

An embodiment of the present invention further provides a method for expressing a multivalent polymer on a surface including expressing a multivalent polymer on a cell surface from host cells transformed with the aforementioned recombinant expression vector An embodiment of the present invention still further provides a composition for producing nano particles of a multivalent polymer which includes a multimerization peptide domain as an effective ingredient.

The multivalent polymer including a multimerization peptide domain like a hydrophobic tail domain of a hagfish-derived VLRB protein of an embodiment of the present invention exhibits a probe effect by establishing a nano-size by self-assembly, and thus it can be advantageously used in the development of a highly sensitive protein nano chip and the development of a diagnostic kit.

DETAILED DESCRIPTION

Figure 1:
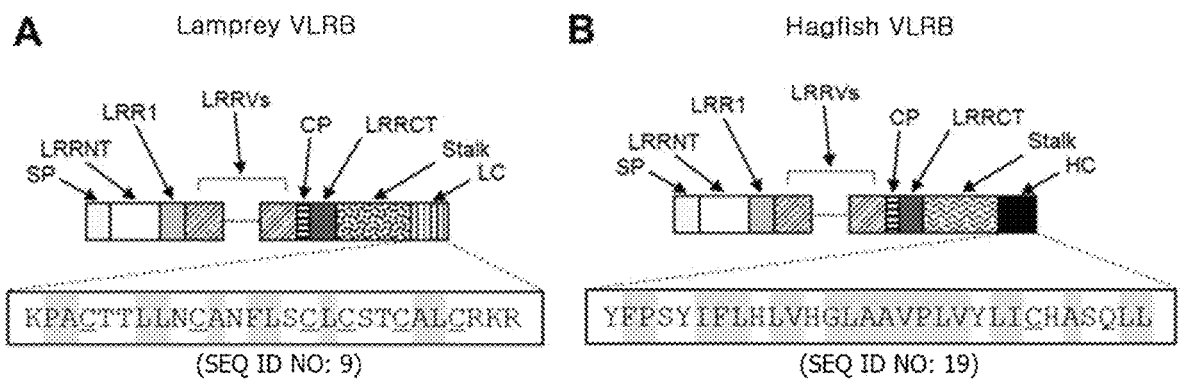
FIG. 1 shows the result of comparing (A) the structure of a lamprey VLRB protein with (B) the structure of a hagfish VLRB protein, in which SP represents a signal peptide; LRRNT represents an N-terminal capped LRR; LRR represents a leucine-rich repeat; LRRVs represents variable LRR modules; CP represents a linking peptide; LRRCT represents a C-terminal capped LRR; LC represents a lamprey carboxy terminal; HC represents a hagfish carboxy terminal; and shaded area in the amino acid sequence represents hydrophobic amino acids.

To achieve the object described above, an embodiment of the present invention provides a multivalent polymer including a multimerization peptide domain and a target protein in which the polymer forms nano particles of a multimer by self-assembly of a monomer.

With regard to the multivalent polymer of the present invention, the multimerization peptide domain can be a hydrophobic tail domain of a VLRB protein, or a peptide domain which forms a dimer, a trimer, a tetramer, a pentamer, a hexamer, a heptamer, an octamer, or a decamer, but it is not limited thereto.

The peptide domain which forms a dimer, a trimer, a tetramer, a pentamer, a hexamer, a heptamer, an octamer, or a decamer can be, although not particularly limited thereto, a leucine zipper domain, an Fc domain of immunoglobulin G, a C-terminal domain of a foldon protein, an Fc domain of immunoglobulin A, an oligomerization domain of C4bp (C4b-binding protein), or a C-terminal domain of lamprey-derived VLRB protein.

With regard to the multivalent polymer according to one embodiment of the present invention, a globular-shaped multimer may be formed when the multimerization peptide domain is a hydrophobic tail domain of a VLRB protein. When the multimerization peptide domain is a leucine zipper domain or an Fc domain of immunoglobulin G, a dimer may be formed. When the multimerization peptide domain is a C-terminal domain of a foldon protein, a trimer may be formed. When the multimerization peptide domain is an Fc domain of immunoglobulin A, a dimer or a tetramer may be formed. When the multimerization peptide domain is a C4bp oligomerization domain, a heptamer may be formed. Furthermore, when the multimerization peptide domain is a C-terminal domain of a lamprey-derived VLRB protein, an octamer or a decamer may be formed.

The hydrophobic tail domain of a hagfish-derived VLRB protein encompasses a polypeptide having the amino acid sequence represented by SEQ ID NO: 1, and functional equivalents of the polypeptide. The term "functional equivalents" indicates a protein having, as a result of addition, substitution, or deletion of an amino acid, at least 70%, preferably at least 80%, more preferably at least 90%, and even more preferably at least 95% sequence homology with the amino acid sequence represented by SEQ ID NO: 1, and it indicates a protein exhibiting substantially the same activity as the protein represented by SEQ ID NO: 1. The expression "substantially the same activity" means the activity of forming nano particles of a multimer by self-assembly.

Furthermore, the leucine zipper domain encompasses the polypeptide having the amino acid sequence of SEQ ID NOs: 2 to 4 and functional equivalents thereof; Fc domain of immunoglobulin G encompasses the polypeptide having the amino acid sequence of SEQ ID NO: 5 and functional equivalents thereof; Fc domain of immunoglobulin A encompasses the polypeptide having the amino acid sequence of SEQ ID NO: 6 and functional equivalents thereof; C-terminal domain of a foldon protein encompasses the polypeptide having the amino acid sequence of SEQ ID NO: 7 and functional equivalents thereof; oligomerization domain of C4bp (C4b-binding protein) encompasses the polypeptide having the amino acid sequence of SEQ ID NO: 8 and functional equivalents thereof; and C-terminal domain of lamprey-derived VLRB protein encompasses the polypeptide having the amino acid sequence of SEQ ID NO: 9 and functional equivalents thereof, and their scope are the same as those described in the above.

As described in the present invention, the "target protein" includes any protein that can be expressed in a trasformant according to incorporation of a polynucleotide encoding the protein to a recombinant expression vector.

In the present invention, any protein desired by a skilled person in the art can be employed as a target protein, and, for example, various foreign proteins with biological activity that are selected from a group consisting of VLR, enzyme, antibody, antigen or part thereof, single chain antibody, cell receptor, binding protein, binding domain, peptide, adhesion protein, structural protein, regulating protein, toxin protein, cytokine, transcription regulating factor, blood coagulating factor, and protein for inducing biophylaxis in plant can be used as a target protein, but it is not limited thereto.

The nano particles are characterized by having a structure in which the multimerization peptide domain is present inside the particle while the target protein protrudes outside the particle.

According to one embodiment of the present invention, the multivalent polymer in which the multimerization peptide domain is a hydrophobic tail domain of a VLRB protein forms globular-shaped nano particles by self-assembly, and, based on size exclusion chromatography and quantitative analysis, it is found that 16 to 42 target proteins can be carried per nano particle. Furthermore, according to observation using an electron microscope, it was found that the multivalent polymer of the present invention forms globular-shaped nano particles which have a diameter of 26 to 31 nm.

In the present invention, the "multivalent polymer" means a protein that is expressed as one polypeptide as a result of linkage of other protein to an amino terminal (N-terminal) or a carboxy terminal (C-terminal) of a sequence of the original target protein or addition of other amino acid to the amino terminal or carboxy terminal.

The multimerization peptide domain may be fused either directly or indirectly to the C-terminal of a target protein, but it is not limited thereto. Preferably, the multimerization peptide domain may be fused to the C-terminal of a target protein.

The present invention further provides a nucleic acid encoding the aforementioned multivalent polymer.

The present invention further provides a recombinant expression vector including the aforementioned nucleic acid encoding the multivalent polymer, and also a host cell transformed with the aforementioned recombinant expression vector.

The term "recombinant" indicates a cell which replicates a heterogeneous nucleotide or expresses said nucleotide, or a peptide, a heterogeneous peptide, or a protein encoded by a heterogeneous nucleotide. Recombinant cell can express a gene or a gene fragment in the form of a sense or antisense, which are not found in natural state of cell. In addition, a recombinant cell can express a gene that is found in natural state, provided that said gene is modified and re-introduced into the cell by an artificial means.

The term "recombinant expression vector" means bacteria plasmid, phage, yeast plasmid, plant cell virus, mammalian cell virus, or other vector. Any plasmid and vector can be generally used if it can replicate and is stabilized in a host. Important characteristics of the expression vector include that it includes a replication origin, a promoter, a marker gene, and a translation control element.

The expression vector including the gene sequence encoding the multivalent polymer of the present invention and an appropriate signal for regulating transcription/translation can be constructed according to a method that is well known to a skilled person in the art. The method includes an in vitro recombinant DNA technique, a DNA synthesis technique, and an in vivo recombinant technique. For inducing mRNA synthesis, the DNA sequence can be effectively linked to a suitable promoter present in the expression vector. In addition, the expression vector may include a ribosome binding site as a translation initiation site and a transcription terminator.

As a host cell with an ability of having stable and continuous cloning and expression of the vector of the present invention in a prokaryotic cell, any host cell known in the pertinent art can be used. Examples of the prokaryotic cells include, *Bacillus* sp. strain including *E. coli* Rosetta, *E. coli* JM109, *E. coli* BL21, *E. coli* RR1, *E. coli* LE392, *E. coli* B, *E. coli* X 1776, *E. coli* Da, *E. coli* W3110, *Bacillus subtillus, Bacillus thuringiensis* and the like, and intestinal bacteria and strains including *Salmonella typhimurium, Serratia marcescens* and various *Pseudomonas* sp. etc.

Furthermore, when an eukaryotic cell is transformed with the vector of the present invention, yeast (*Saccharomyce cerevisiae*), an insect cell, a human cell and an animal cell (for example, CHO (Chinese hamster ovary), W138, BHK, COS-7, 293, HepG2, 3T3, RIN, and MDCK cell line), a plant cell, and the like can be used as a host cell.

The present invention further provides a method for producing a multivalent polymer forming nano particles, including:
1) preparing a recombinant expression vector including a nucleic acid encoding a multivalent polymer;
2) culturing a host cell transformed with the recombinant expression vector; and
3) obtaining the multivalent polymer forming nano particles from the cultured host cell.

The present invention further provides a method for expressing a multivalent polymer on a cell surface including:
1) preparing a recombinant expression vector including a nucleic acid encoding a multivalent polymer;
2) culturing a host cell transformed with the recombinant expression vector; and
3) expressing the multivalent polymer on a surface of the cultured host cell.

The present invention still further provides a composition for producing nano particles of a multivalent polymer which includes the multimerization peptide domain as an effective ingredient. The composition for producing nano particles of a multivalent polymer of the present invention includes the multimerization peptide domain as an effective ingredient, and, according to binding of a target protein to the multimerization peptide domain, nano particles of a multimer of a target protein can be produced.

With regard to the composition of the present invention, the multimerization peptide domain is the same as those described in the above.

Hereinbelow, the present invention is explained in greater detail in view of the Examples. However, it is evident that the following Examples are given only for exemplification of the present invention and by no means the present invention is limited to the following Examples.

EXAMPLES

Materials and Methods

1. Animals and Cells Used for Experiments

Hagfish (inshore hagfish, *Eptatretus burgeri*) with a size of 20 to 30 cm was obtained from a local fisherman, and kept in an aquarium at 14 to 15° C. After anesthetization by immersing the fish in 0.1 g/f, ethyl 3-aminobenzoate methanesulfonic acid, whole blood was collected and diluted in 0.67×PBS (phosphate-buffered saline) containing 10 mM EDTA (ethylenediaminetetraacetic acid) in the same amount as the blood. According to centrifuge for 10 minutes at 500×g, blood plasma was obtained. Protein assay was carried out by using Pierce BCA protein assay kit (Thermo Scientific, USA). HEK (human embryonic kidney) 293-F cells were obtained from Gibco (USA), and cultured at 37° C. by using DMEM (Dulbecco's Modified Eagle's Media) in which 10% FBS (fetal bovine serum) is contained.

2. Western Blotting

The hagfish blood plasma sample (3.5 µg/lane) was separated by 8% native-PAGE or 12% SDS-PAGE under non-reducing conditions, and, after transfer of the protein onto a PVDF membrane, the hagfish VLRB protein was identified according to a reaction with a mouse anti-VLRB antibody which recognizes the constant stalk region of a hagfish VLRB protein. In order to determine the disruption of the conjugate VLRB by a surfactant, the hagfish blood plasma sample was treated with SDS (sodium dodecyl sulfate) at concentration of 0, 0.003, 0.01, 0.03, 0.1, or 0.3% (v/v) and reacted for 10 minutes at room temperature. After that, Western blotting was carried out according to the aforementioned method.

3. Size Exclusion Chromatography and Immunoblotting

The hagfish blood plasma sample (100 µg) diluted in 600 µl PBS was filleted through a 0.2 µm membrane and applied to Superdex 200 10/300 GL (GE Healthcare, England), and then chromatography was carried out. In order to identify a fraction containing VLRB from the hagfish blood plasma, dot blotting was carried out by using each fraction which is eluted every minute. Because the eluted fractions showed a weak signal in dot blotting, the fractions were concentrated 10 times by freeze-drying and dot blotting was carried out again by using the concentrated sample. After selecting the eluted fraction samples exhibiting a strong signal, Western blotting was carried out.

4. Transmission Electron Microscopy

By using PBS, 100-fold dilution of the fractionated hagfish VLRB (eluted at 16-minute to 17-minute) samples was carried out to prepare them at final concentration of 50 nM. 5 µl of the sample was applied on a carbon-coated grid and subjected to glow-discharge for 3 minutes in air. After that, the grid was immediately subjected to negative staining by using 1% uranyl acetate. For immunogold labeled electron microscope analysis, the fractionated 50 nM sample of hagfish VLRBs was admixed with a mouse anti-VLRB antibody (11G5) at a ratio of 1:2, and, after allowing them to react for 1 hour, a treatment with a secondary antibody bound with gold nano particles was carried out. After the reaction overnight on ice, negative staining was carried out in the same manner as above. Prepared samples were observed by using Tecnai T10 transmission electron microscope (FEI, USA).

5. Plasmid Construction

Mammalian expression vector pTracer-EF/V5-His (Invitrogen Life Technologies, USA) was partially modified to introduce murine Ig κ chain leader sequence and two SfiI sites. Finally, pKINGeo/ccdB introduced with two murine Ig κ chain leader sequences, two SfiI sites, and ccdB gene as a chloramphenicol resistant gene was produced. In order to analyze the characteristic of the hydrophobic carboxy terminal of a hagfish VLRB protein, a mutant having serial deletion of the hydrophobic carboxy terminal of a hagfish VLRB and a reporter gene was prepared with the pKINGeo/ccdB vector followed by cloning.

6. Flow Cytometry and Confocal Microscopy

HEK 293-F cells were cultured up to 90% or so in a 6-well plate, and each plasmid was admixed with lipofectamine 2000 (Invitrogen, USA) according to the manufacturer's instruction and then added to the cells. After 4 hours, the cell culture medium was replaced with fresh medium, and the cells were further cultured for 48 hours. After that, the transfected cells were collected, reacted with mouse anti-VLRB antibody (11G5), and then subjected to cell analysis by using FACS Calibur™ (BD Biosciences, USA).

In addition, HEK 293-F cells were cultured up to 70% or so on a 8-chamber slide, and then transfected with the plasmid as described in the above. The transfected cells were fixed with 4% paraformaldehyde, and, after blocking for 30 minutes with PBS added with 0.1% BSA (bovine serum albumin), a reaction with mouse anti-VLRB antibody (11G5) was allowed to occur so as to have a reaction with FITC-labeled anti-mouse IgG antibody for 30 minutes. The final slide was subjected to cell image analysis by using Zeiss Axiovert confocal microscope (Zeiss, Germany).

7. Treatment with Phospholipase C

Two days after introducing the plasmid expressing RFP-stalk or RFP-stalk-HC to HEK 293-F cells, the cells were treated with bacteria GPI (glycosylphosphatidylinositol)-specific phospholipase C at concentration of 1 unit/ml or 3 units/ml. After reacting them for 45 minutes at 30° C., the cells were collected. Then, the phospholipase C-treated cells were reacted with anti-VLRB antibody (11G5) and treated with FITC-labeled anti-mouse IgG antibody as a secondary antibody, and then flow cytometry was carried out.

Example 1. Determination of VLRB Present as Multimer Complex in Hagfish Blood Plasma The VLRB protein structure of a hagfish and a lamprey consists of a signal peptide (SP), LRRNT (N-terminal capped LRR), LRR1, LRRVs (variable LRR modules), CP (connecting peptide), LRRCT (C-terminal capped LRR), stalk, and a carboxy terminal (C-terminal) as shown in FIG. 1, and the U-shaped tertiary structure is very similar between the hagfish and lamprey. The C-terminal of a lamprey has 8 cysteine (Cys) residues, and thus, as it has been reported before, it forms a VLRB complex of about 400 kDa according to clustering of 8 to 10 monomers, and is expressed on a cell surface and also secreted into blood plasma. On the other hand, it was found that the C-terminal of the hagfish VLRB consists of amino acids having high hydrophobicity (FIG. 1).

To determine the natural state of a hagfish VLRB in blood plasma, the extracted blood plasma protein was separated by native-PAGE or SDS-PAGE, and then, by using anti-VLRB antibody (11G5) capable of detecting the stalk domain of hagfish VLRB, which has been developed in previous studies, Western blotting was carried out. Accordingly, it was found that the all VLRB proteins are present in the stacking gel when the hagfish blood plasma proteins are separated by native-PAGE. On the other hand, from the hagfish blood plasma which has been treated with SDS at various concentrations, each VLRB protein was separated in monomer form, and separated at molecular weight of about 40 kDa (FIGS. 2A and 2B). Based on those results, it was able to confirm that, in natural state, the hagfish VLRB protein forms a multimer based on hydrophobic interaction, and the protein is separated in monomer form when treated with a surfactant that can remove the hydrophobic interaction.

Figure 2:
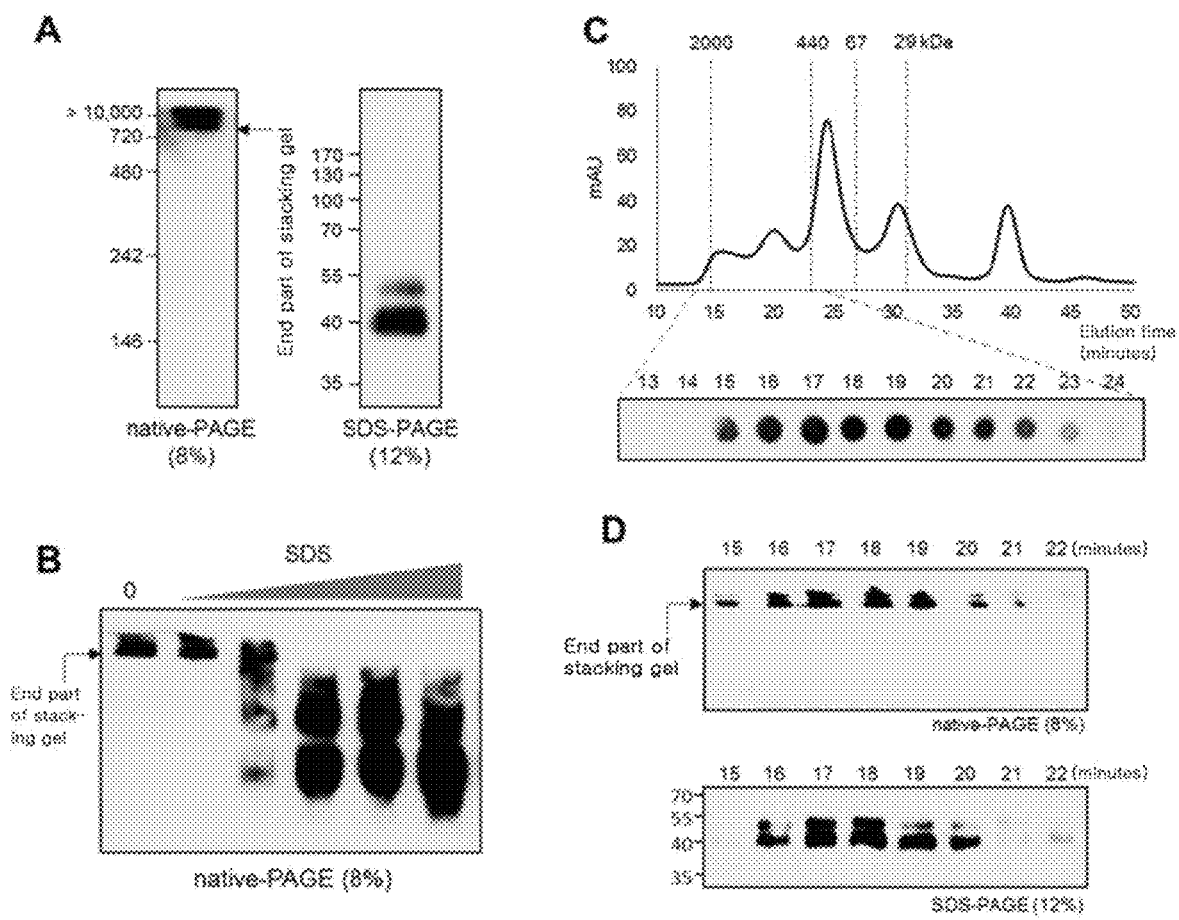
FIG. 2 shows the result of determination of a VLRB protein in hagfish blood plasma, in which A of FIG. 2 shows the result of Western blotting of the VLRB protein based on native-PAGE or SDS-PAGE; B of FIG. 2 shows the result of Western blotting of the VLRB protein from blood plasma proteins treated with SDS at various concentrations; C of FIG. 2 shows the fractionation of a hagfish blood plasma sample in accordance with a protein size and the result of dot blotting of the VLRB protein separated from each fraction; and D of FIG. 2 shows the result of Western blotting of the VLRB protein separated from each fraction.
Figure 3:
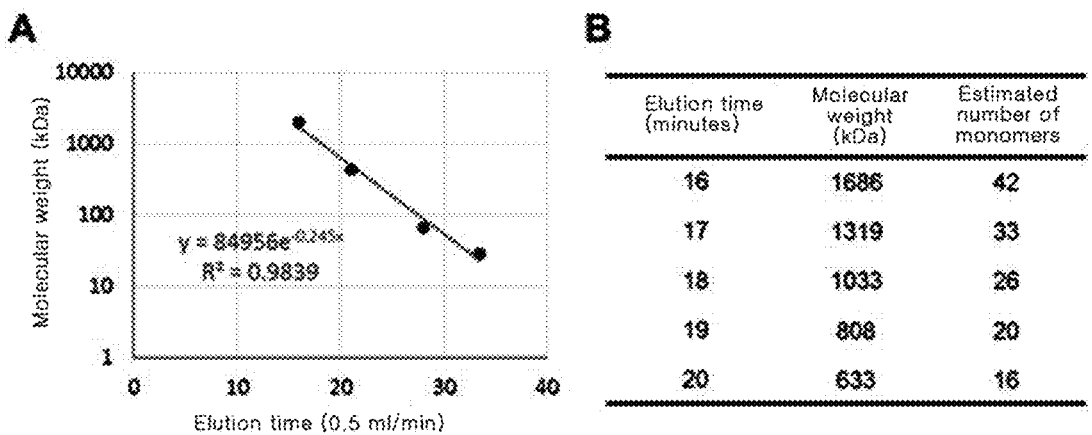
FIG. 3 shows (A) molecular weight curve of a standard sample of a hagfish blood plasma fraction in which the molecular weight is plotted against elution time, and (B) estimated number of monomers of a VLRB complex which has been eluted in each fraction.

In order to separate the blood plasma proteins in accordance with a molecular size, size exclusion chromatography was carried out, and, as a result of performing dot blotting of the eluted fraction samples that are obtained according to each elution time (i.e., 1 to 48 minutes, 0.5 ml/minute) by using hagfish VLRB-specific antibody (11G5), presence of the VLRB protein was found from the fractions that are obtained 15 to 23 minutes after starting the elution (C of FIG. 2). Furthermore, as a result of determining the each obtained fraction by native-PAGE and SDS-PAGE using 11G5, presence of the hagfish VLRB was shown (D of FIG. 2). In particular, the VLRB proteins were shown in the largest amount between 16 and 20 minutes after starting the elution, and, when the molecular weight of the eluted VLRB proteins is estimated based on Ferguson plot, it is found that the hagfish VLRB protein is present in the form of a huge protein complex with a size of about 600 to 1,700 kDa (FIG. 3). When calculation is carried out against the corresponding VLRB monomer with a size of about 40 kDa, it is recognized that the VLRB complex is present as a multimer resulting from clustering of about 16 to 42 VLRB protein monomers, in which the clustering is caused by the hydrophobic part at the C-terminal.

Figure 4:
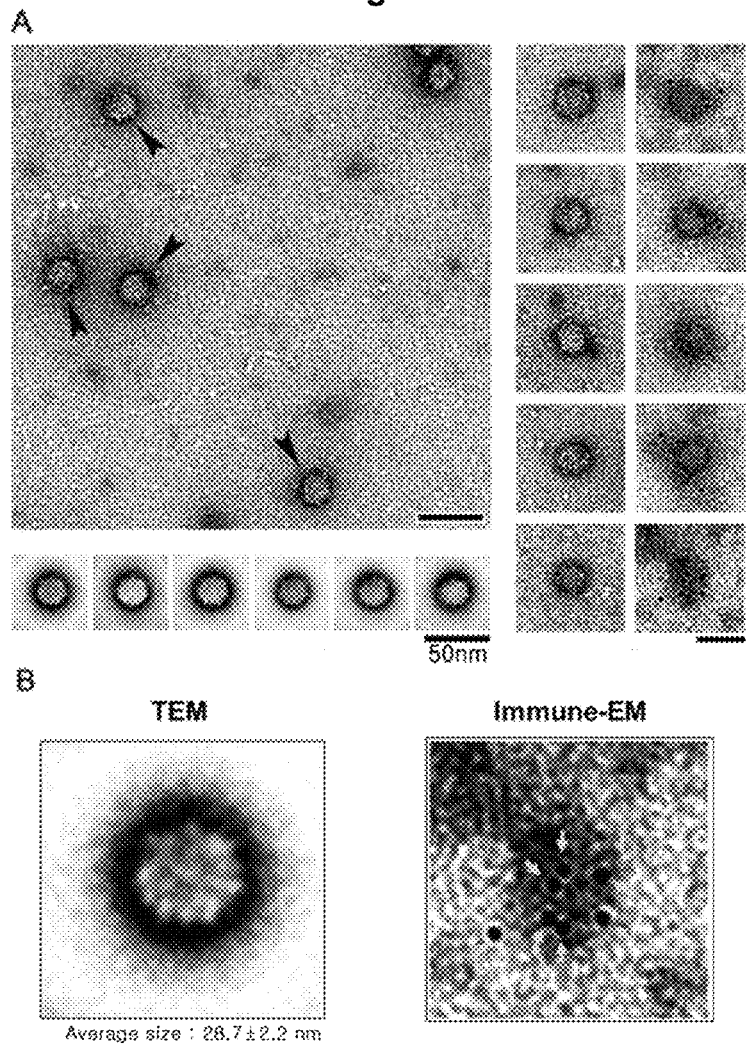
FIG. 4 shows (A) the result of an actual VLRB image analysis of 16-minute and 17-minute fractions that have been separated, based on size, by FPLC as a major population from the VLRB fractions, in which the image analysis was carried out by negatively stained TEM, and (B) the result of determining the VLRB by using 11G5 as a VLRB-specific antibody and detecting the VLRB by a gold-labeled secondary antibody.

Actual image of the VLRB protein complex separated by the size exclusion chromatography described above was examined under a transmission electron microscope (TEM). Fractions of 16-minute and 17-minute, which have been separated as a major population from the VLRB fractions separated according to a size by FPLC (fast protein liquid chromatography), were subjected to analysis of actual VLRB image by negatively stained TEM. As a result, it was observed that the fractions are present as a globular-shaped protein mass with a size of 28.7±2.2 nm (FIG. 4). In particular, white color of the central core of the globular-shaped particle indicates that the hydrophobic clustering is present inside. Furthermore, by using 11G5 as a hagfish VLRB specific antibody and also gold-labeled secondary antibody, VLRB was detected to verify the result (FIG. 4).

Figure 5:
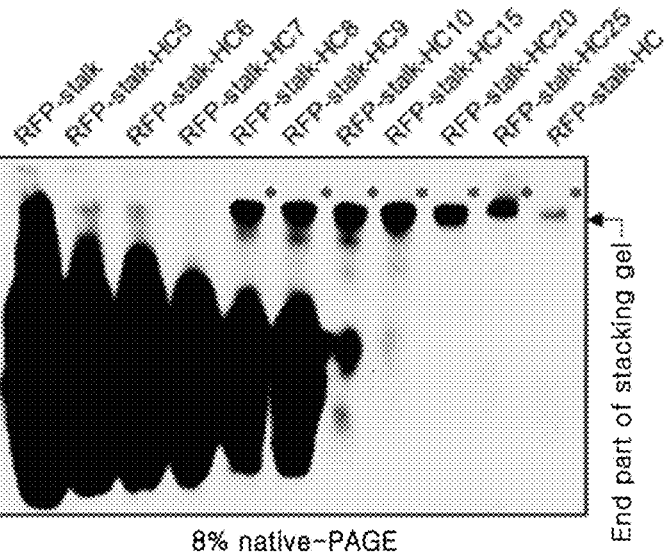
FIG. 5 shows the result of Western blotting based on (A) native-PAGE or (B) SDS-PAGE of a recombinant VLRB protein which has been obtained by fusion of a hagfish C-terminal fragment (30 amino acids) to the terminal of RFP-stalk and expression of the fusion product in 293-F cell line, in which the fusion has been made for each different size (i.e., 5, 6, 7, 8, 9, 10, 15, 20, 25, and 30).

Example 2. Determination of Multimer Forming and Cell Surface Expression of Fluorescent Protein Including Hagfish VLRB Carboxy Terminal In order to examine whether or not the hydrophobic carboxy terminal of a hagfish VLRB protein (SEQ ID NO: 1) is an actual element required for forming the multimer, the nucleotide sequence from stalk region to carboxy terminal of a VLRB protein was linked to RFP (red fluorescent protein) gene followed by cloning. Furthermore, mutants having serial deletion of the hydrophobic terminal (HC) of the hagfish VLRB protein were prepared (Table 1), and expressed in HEK 293-F cell line. As a result, both the RFP-stalk and RFP-stalk-HC5 proteins were observed in monomer form, but, content of the protein in monomer form decreases as the hydrophobic terminal (HC) of the VLRB protein increases, while the multimer is produced in higher amount (FIG. 5). The multimer was formed first from the RFP-stalk-HC8 protein, and only the complete multimer was produced from the RFP-stalk-HC15 and thereafter.

TABLE 1

RFP-stalk and RFP-stalk-HC Fusion proteins

| Name | Signal peptide | Reporter protein | Hagfish hydrophobic Stalktail (HC) |
|---|---|---|---|
| RFP-stalk | IgK | RFP | Stalk— |
| RFP-stalk-HC5 | | | YFPSY (SEQ ID No: 10) |
| RFP-stalk-HC6 | | | YFPSYI (SEQ ID No: 11) |
| RFP-stalk-HC7 | | | YFPSYIF (SEQ ID No: 12) |
| RFP-stalk-HC8 | | | YFPSYIFL (SEQ ID No: 13) |
| RFP-stalk-HC9 | | | YFPSYIFLH (SEQ ID No: 14) |
| RFP-stalk-HC10 | | | YFPSYIFLHL ((SEQ ID No: 15) |
| RFP-stalk-HC15 | | | YFPSYIFLHLVHGLA (SEQ ID No: 16) |
| RFP-stalk-HC20 | | | YFPSYIFLHLVHGLAAVPLV (SEQ ID No: 17) |
| RFP-stalk-HC25 | | | YFPSYIFLHLVHGLAAVPLVYLICH (SEQ ID No: 18) |
| RFP-stalk-HC | | | YFPSYIFLHLVHGLAAVPLVYLICHASQLL (SEQ ID No: 19) |

Figure 6:
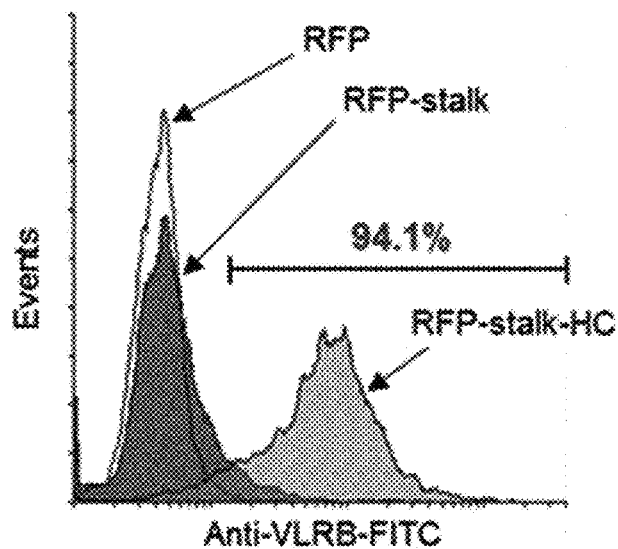
FIG. 6 shows the result of determining the expression site of a recombinant protein in an extracellular membrane expressing RFP, RFP-stalk, or RFP-stalk-HC, in which the determination was made based on flow cytometry.

To examine whether or not the fusion protein is actually expressed on a cell surface, flow cytometry was carried out by using a specific antibody which recognizes the stalk region of a VLRB protein. As a result, it was found that the VLRB proteins are displayed on a surface of cells in higher number than the negative control. It was also found that the proteins are present only on a surface of HEK 293-F cells that are transformed with RFP-stalk-HC containing the hydrophobic terminal (HC) region (FIG. 6).

Figure 7:
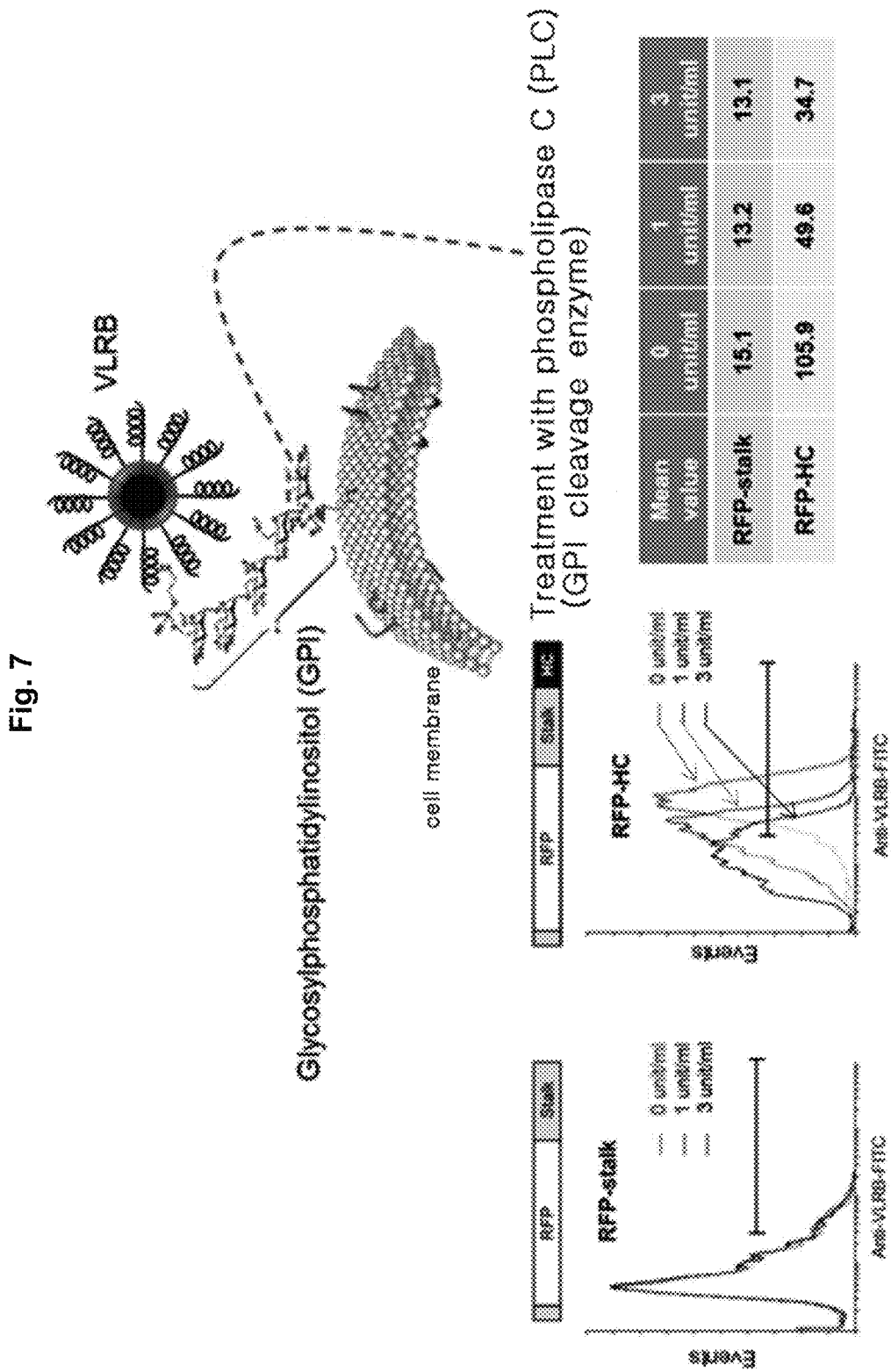
FIG. 7 shows the hydrolysis of the bond of RFP-stalk-HC protein which is linked to, via GPI linkage, an outside of the cell membrane, when RFP-stalk or RFP-stalk-HC was expressed in 293-F cell line and then treated with phospholipase C (PLC) enzyme at different concentrations, i.e., 1 unit/ml and 3 unit/ml, in which the hydrolysis was determined by flow cytometry.

It was found that the RFP-stalk-HC prepared by linking the HC to RFP-stalk gene can be expressed in HEK 293-F cell line and secreted in polymer form to the outside of a cell, and it was also found that the form displayed on the outside of an extracellular membrane is linked by GPI (glycosylphosphatidylinositol). It was found by flow cytometry analysis that, when RFP-stalk and RFP-stalk-HC are expressed in 293-F cell line and then treated with PLC (phospholipase C) enzyme at concentration of 1 unit/ml or 3 unit/ml, the RFP-stalk that is not present on the outside of a cell membrane is not affected at all by the treatment, but the RFP-stalk-HC protein linked to the outside of a cell membrane via GPI undergoes the hydrolysis of protein bonds by PLC (FIG. 7).

Figure 8:
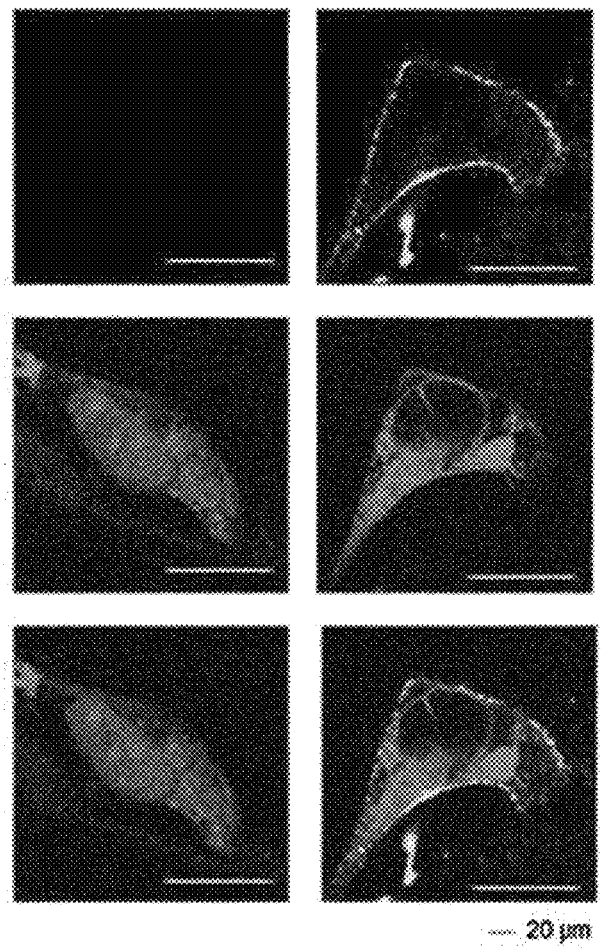
FIG. 8 shows the result of determining the expression site of a recombinant protein in cells expressing RFP-stalk or RFP-stalk-HC, in which the determination was made based on an immunocytochemical assay.

To further examine that the RFP protein linked with the entire hydrophobic terminal region of a hagfish (i.e., RFP-stalk-HC) is secreted to the outside of a cell and also displayed on a cell surface before secretion like mammalian IgG and IgM, observation under a confocal microscopy was carried out. In order to examine the transfection, the expression vector system includes an expression site for GPF protein other than RFP. It was observed that the proteins are accumulated on cell surface only in 293-F cells which have been transfected with the RFP-stalk-HC (FIG. 8).

Figure 9:
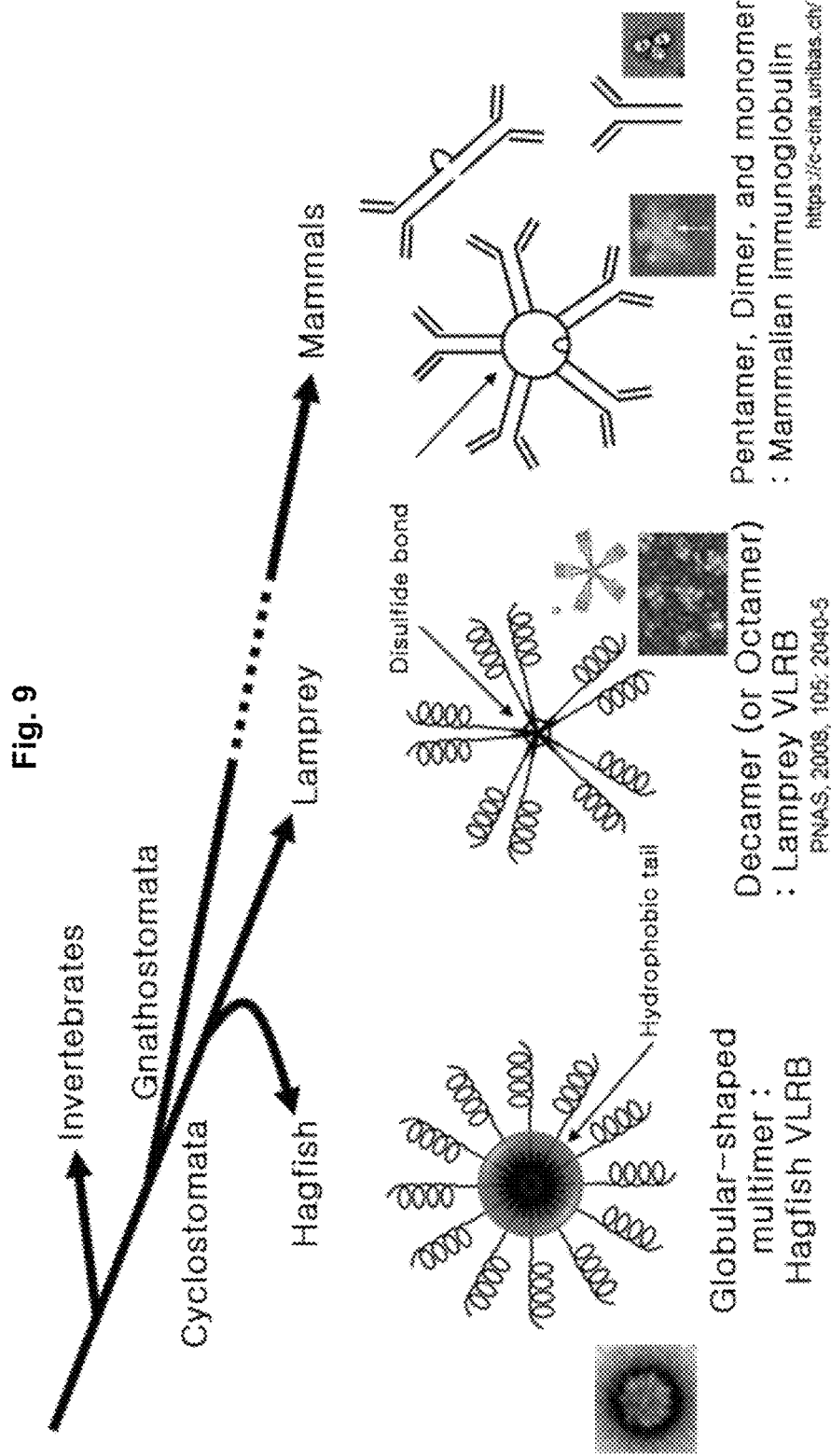
FIG. 9 shows comparison of the structural relationship among hagfish VLRB, lamprey VLRB, and immunoglobulin antibody.

It was found that based on the above results, after the expression, the hagfish VLRB protein is secreted in globular-shaped complex form to the outside of a cell, i.e., into blood, and secreted in the form that is completely different from the pentamer structure of a lamprey (FIG. 9). Namely, it was shown that the hagfish VLRB protein has an antibody structure with specific shape that has never been found in mammals or other species.

Example 3. Production of Various Multimer Forms of Hagfish Antibody

The inventors of the present invention produced various forms of a hagfish antibody by substituting the entire hydrophobic terminal part of a hagfish VLRB protein (i.e., amino acid sequence of SEQ ID No: 1) with a multimerization peptide domain. The multimerization peptide domain used in the present invention is as follows: leucine zipper domain (amino acid sequence of SEQ ID NOs: 2 to 4), Fc domain of mouse immunoglobulin G (amino acid sequence of SEQ ID NO: 5), Fc domain of mouse immunoglobulin A (amino acid sequence of SEQ ID NO: 6), C-terminal domain of a foldon protein (amino acid sequence of SEQ ID NO: 7), oligomerization domain of C4bp (C4b-binding protein) (amino acid sequence of SEQ ID NO: 8), and C-terminal domain of lamprey-derived VLRB protein (amino acid sequence of SEQ ID NO: 9).

Figure 10:
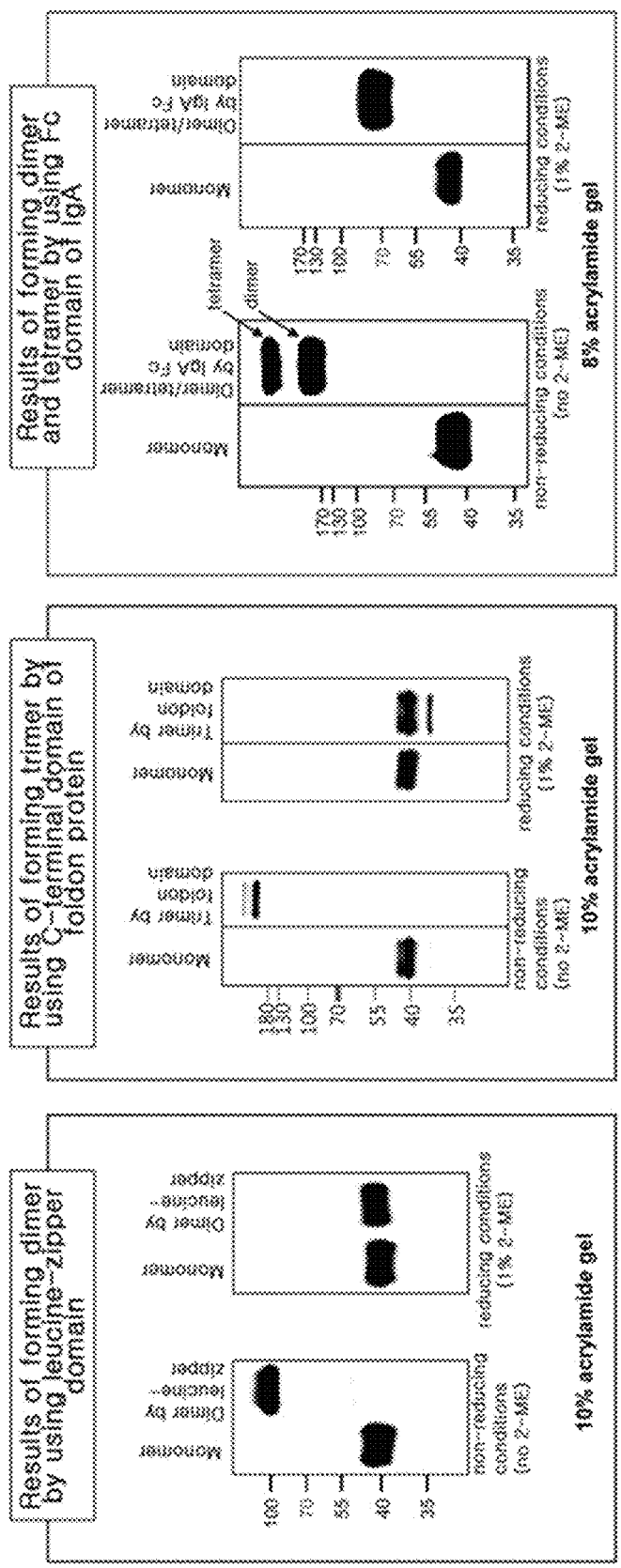
FIG. 10 shows the result of Western blotting of a hagfish VLRB multimer under reducing and non-reducing conditions, in which the hagfish VLRB multimer has been produced by using a leucine zipper domain, C-terminal domain of a foldon protein, or a Fc domain of immunoglobulin A.
Figure 11:
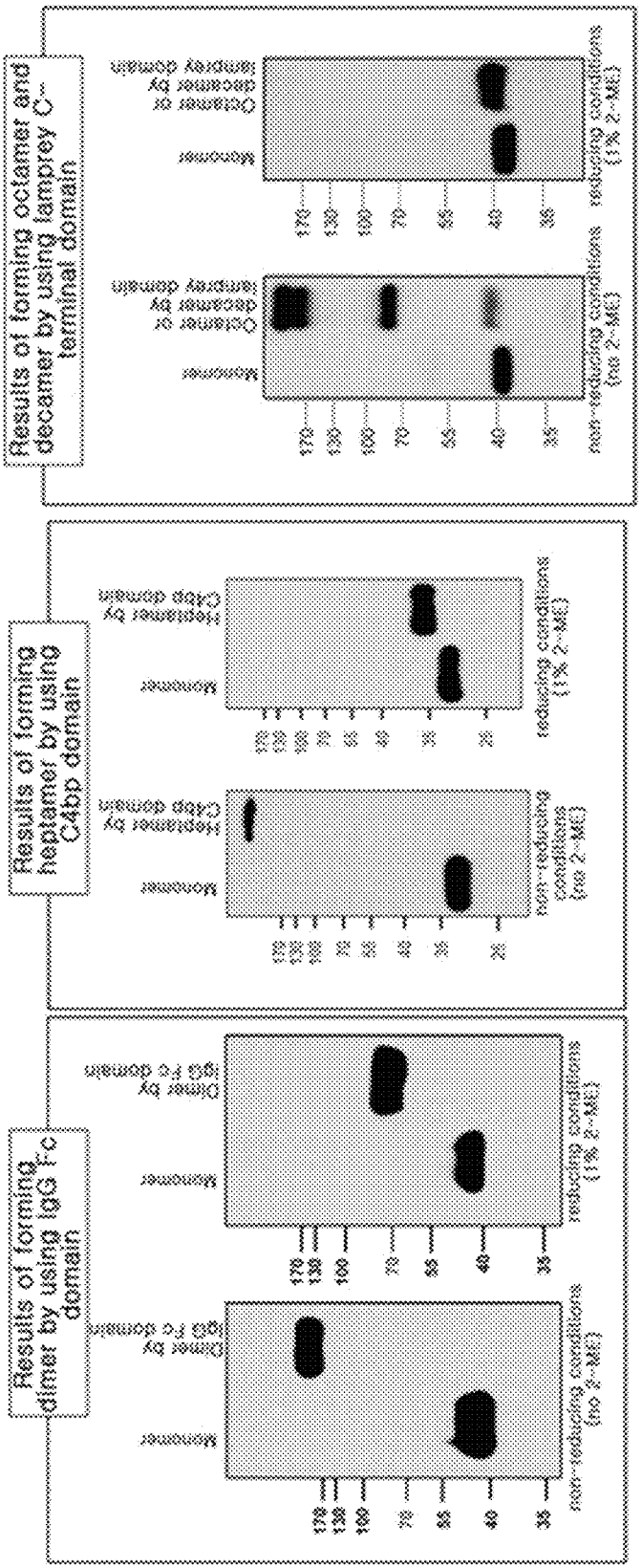
FIG. 11 shows the result of Western blotting of a hagfish VLRB multimer under reducing and non-reducing conditions, in which the hagfish VLRB multimer has been produced by using a Fc domain of immunoglobulin G, an oligomerization domain of C4bp (C4b-binding protein), or a C-terminal domain of lamprey-derived VLRB protein.
Figure 12:
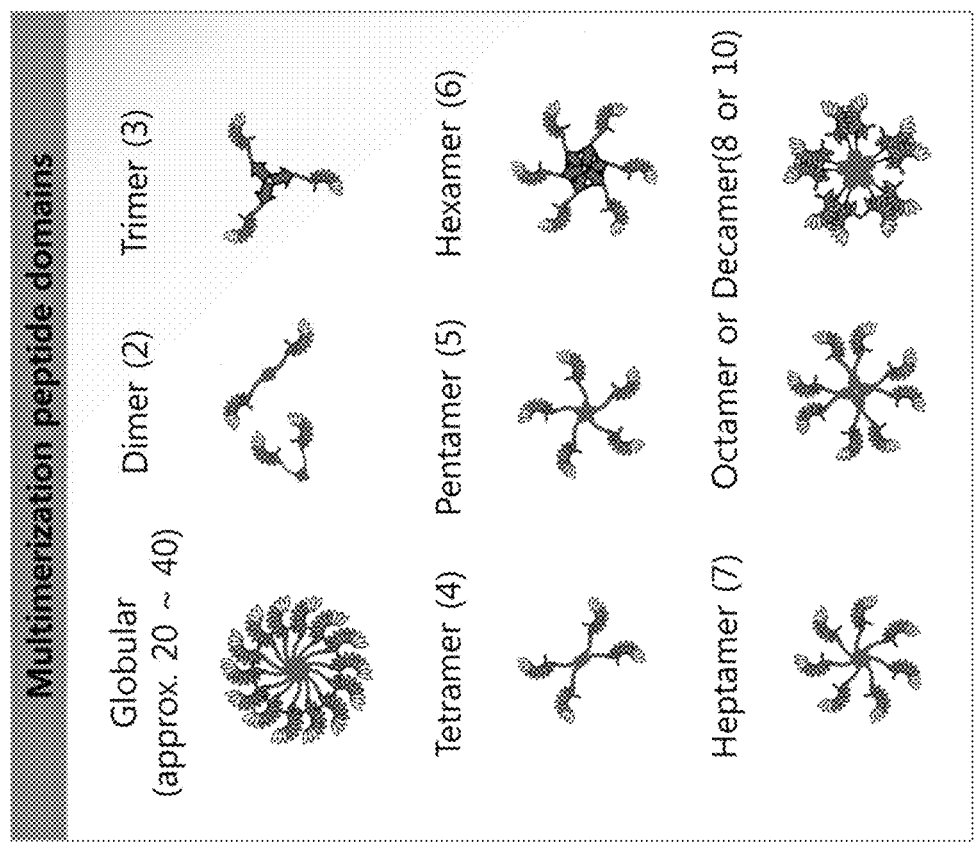
FIG. 12 is a schematic diagram showing the hagfish VLRB multimer in which multimerization peptide domain is employed.

A recombinant protein resulting from substitution of the entire hydrophobic terminal part of a hagfish VLRB protein with other multimerization peptide domain was expressed in 293-F, which is human embryonic kidney cell line. After that, as a result of analyzing the shape of the protein under non-reducing conditions in which a treatment with β-mercaptoethanol is not carried out or under reducing conditions in which a treatment with β-mercaptoethanol is carried out, it was recognized that the protein is in multimer form under non-reducing conditions while it is fully separated in monomer form under reducing conditions (FIG. 10 and FIG. 11).

What are claimed are:

1. A multivalent polymer comprising:
a multimerization peptide domain comprising:
a hydrophobic tail domain of a variable lymphocyte receptor B (VLRB) having the amino acid sequence represented by SEQ ID NO: 1; and
a target protein fused directly or indirectly with the multimerization peptide domain, wherein the target protein is a protein different from the variable lymphocyte receptor B (VLRB),
wherein the multivalent polymer is in a form of nanoparticles of a multimer.

2. The multivalent polymer of claim 1, wherein the target protein is a variable lymphocyte receptor (VLR) different from the variable lymphocyte receptor B (VLRB), an antigen, an antibody, a cell receptor, or an enzyme.

3. The multivalent polymer of claim 1, wherein the nanoparticles have a structure in which the multimerization peptide domain is present inside the nanoparticles while the target protein protrudes outside the nanoparticles.

4. The multivalent polymer of claim 1, wherein the multimerization peptide domain is fused to the C-terminal of the target protein.

5. The multivalent polymer of claim 1, wherein the target protein is selected from the group consisting of an antigen, an antibody, a cell receptor, and an enzyme,
wherein the nanoparticles have a structure in which the hydrophobic tail domain is present inside the nanoparticles while the target protein protrudes outside the nanoparticles; and
the multimer has a size of about 600 to 1,700 kDa.

* * * * *

SEQUENCE LISTING

```
<160> NUMBER OF SEQ ID NOS: 19

<210> SEQ ID NO 1
<211> LENGTH: 30
<212> TYPE: PRT
<213> ORGANISM: Eptatretus burgeri

<400> SEQUENCE: 1

Tyr Phe Pro Ser Tyr Ile Phe Leu His Leu Val His Gly Leu Ala Ala
1               5                   10                  15

Val Pro Leu Val Tyr Leu Ile Cys His Ala Ser Gln Leu Leu
            20                  25                  30

<210> SEQ ID NO 2
<211> LENGTH: 33
<212> TYPE: PRT
<213> ORGANISM: Homo sapiens

<400> SEQUENCE: 2

Arg Met Lys Gln Leu Glu Asp Lys Val Glu Glu Leu Leu Ser Lys Asn
1               5                   10                  15

Tyr His Leu Glu Asn Glu Val Ala Arg Leu Lys Lys Leu Val Gly Glu
            20                  25                  30

Arg

<210> SEQ ID NO 3
<211> LENGTH: 31
<212> TYPE: PRT
<213> ORGANISM: Homo sapiens

<400> SEQUENCE: 3

Lys Gln Ile Glu Asp Lys Leu Glu Glu Ile Leu Ser Lys Leu Tyr His
1               5                   10                  15

Ile Glu Asn Glu Leu Ala Arg Ile Lys Lys Leu Leu Gly Glu Arg
            20                  25                  30

<210> SEQ ID NO 4
<211> LENGTH: 31
```

```
<212> TYPE: PRT
<213> ORGANISM: Homo sapiens

<400> SEQUENCE: 4

Lys Gln Ile Glu Asp Lys Ile Glu Glu Ile Leu Ser Lys Ile Tyr His
1               5                   10                  15

Ile Glu Asn Glu Ile Ala Arg Ile Lys Lys Leu Ile Gly Glu Val
            20                  25                  30

<210> SEQ ID NO 5
<211> LENGTH: 222
<212> TYPE: PRT
<213> ORGANISM: Mus musculus

<400> SEQUENCE: 5

Gly Cys Lys Pro Cys Ile Cys Thr Val Pro Glu Val Ser Ser Val Phe
1               5                   10                  15

Ile Phe Pro Pro Lys Pro Lys Asp Val Leu Thr Ile Thr Leu Thr Pro
            20                  25                  30

Lys Val Thr Cys Val Val Val Asp Ile Ser Lys Asp Asp Pro Glu Val
        35                  40                  45

Gln Phe Ser Trp Phe Val Asp Asp Val Glu Val His Thr Ala Gln Thr
    50                  55                  60

Gln Pro Arg Glu Glu Gln Phe Asn Ser Thr Phe Arg Ser Val Ser Glu
65                  70                  75                  80

Leu Pro Ile Met His Gln Asp Trp Leu Asn Gly Lys Glu Phe Lys Cys
                85                  90                  95

Arg Val Asn Ser Ala Ala Phe Pro Ala Pro Ile Glu Lys Thr Ile Ser
            100                 105                 110

Lys Thr Lys Gly Arg Pro Lys Ala Pro Gln Val Tyr Thr Ile Pro Pro
        115                 120                 125

Pro Lys Glu Gln Met Ala Lys Asp Lys Val Ser Leu Thr Cys Met Ile
    130                 135                 140

Thr Asp Phe Phe Pro Glu Asp Ile Thr Val Glu Trp Gln Trp Asn Gly
145                 150                 155                 160

Gln Pro Ala Glu Asn Tyr Lys Asn Thr Gln Pro Ile Met Asp Thr Asp
                165                 170                 175

Gly Ser Tyr Phe Val Tyr Ser Lys Leu Asn Val Gln Lys Ser Asn Trp
            180                 185                 190

Glu Ala Gly Asn Thr Phe Thr Cys Ser Val Leu His Glu Gly Leu His
        195                 200                 205

Asn His His Thr Glu Lys Ser Leu Ser His Ser Pro Gly Lys
    210                 215                 220

<210> SEQ ID NO 6
<211> LENGTH: 242
<212> TYPE: PRT
<213> ORGANISM: Mus musculus

<400> SEQUENCE: 6

Gly Cys Lys Pro Cys Ile Cys Thr Val Pro Glu Val Ser Ser Val Phe
1               5                   10                  15

Ile Phe Pro Pro Lys Pro Lys Asp Val Leu Thr Ile Thr Leu Thr Pro
            20                  25                  30

Lys Val Thr Cys Val Val Val Asp Ile Ser Lys Asp Asp Pro Glu Val
        35                  40                  45

Gln Phe Ser Trp Phe Val Asp Asp Val Glu Val His Thr Ala Gln Thr
```

```
                    50                  55                  60
Gln Pro Arg Glu Glu Gln Phe Asn Ser Thr Phe Arg Ser Val Ser Glu
 65                  70                  75                  80

Leu Pro Ile Met His Gln Asp Trp Leu Asn Gly Lys Glu Phe Lys Cys
                 85                  90                  95

Arg Val Asn Ser Ala Ala Phe Pro Ala Pro Ile Glu Lys Thr Ile Ser
                100                 105                 110

Lys Thr Lys Gly Arg Pro Lys Ala Pro Gln Val Tyr Thr Ile Pro Pro
            115                 120                 125

Pro Lys Glu Gln Met Ala Lys Asp Lys Val Ser Leu Thr Cys Met Ile
        130                 135                 140

Thr Asp Phe Phe Pro Glu Asp Ile Thr Val Glu Trp Gln Trp Asn Gly
145                 150                 155                 160

Gln Pro Ala Glu Asn Tyr Lys Asn Thr Gln Pro Ile Met Asp Thr Asp
                165                 170                 175

Gly Ser Tyr Phe Val Tyr Ser Lys Leu Asn Val Gln Lys Ser Asn Trp
            180                 185                 190

Glu Ala Gly Asn Thr Phe Thr Cys Ser Val Leu His Glu Gly Leu His
        195                 200                 205

Asn His His Thr Glu Lys Ser Leu Ser His Ser Pro Gly Lys Thr Ser
    210                 215                 220

Pro Thr Asn Val Ser Val Ser Val Ile Met Ser Glu Gly Asp Gly Ile
225                 230                 235                 240

Cys Tyr
```

<210> SEQ ID NO 7
<211> LENGTH: 27
<212> TYPE: PRT
<213> ORGANISM: Unknown
<220> FEATURE:
<223> OTHER INFORMATION: T4 bacteriophage

<400> SEQUENCE: 7

```
Gly Tyr Ile Pro Glu Ala Pro Arg Asp Gly Gln Ala Tyr Val Arg Lys
 1               5                  10                  15

Asp Gly Glu Trp Val Leu Leu Ser Thr Phe Leu
                20                  25
```

<210> SEQ ID NO 8
<211> LENGTH: 58
<212> TYPE: PRT
<213> ORGANISM: Homo sapiens

<400> SEQUENCE: 8

```
Trp Glu Thr Pro Glu Gly Cys Glu Gln Val Leu Thr Gly Lys Arg Leu
 1               5                  10                  15

Met Gln Cys Leu Pro Asn Pro Glu Asp Val Lys Met Ala Leu Glu Val
                20                  25                  30

Tyr Lys Leu Ser Leu Glu Ile Glu Gln Leu Glu Leu Gln Arg Asp Ser
            35                  40                  45

Ala Arg Gln Ser Thr Leu Asp Lys Glu Leu
        50                  55
```

<210> SEQ ID NO 9
<211> LENGTH: 27
<212> TYPE: PRT
<213> ORGANISM: Lampetra japonica -continued

<400> SEQUENCE: 9

Lys Pro Ala Cys Thr Thr Leu Leu Asn Cys Ala Asn Phe Leu Ser Cys
1               5                   10                  15

Leu Cys Ser Thr Cys Ala Leu Cys Arg Lys Arg
            20                  25

<210> SEQ ID NO 10
<211> LENGTH: 5
<212> TYPE: PRT
<213> ORGANISM: Artificial Sequence
<220> FEATURE:
<223> OTHER INFORMATION: a RFP-stalk and RFP-stalk-HC Fusion protein

<400> SEQUENCE: 10

Tyr Phe Pro Ser Tyr
1               5

<210> SEQ ID NO 11
<211> LENGTH: 6
<212> TYPE: PRT
<213> ORGANISM: Artificial Sequence
<220> FEATURE:
<223> OTHER INFORMATION: a RFP-stalk and RFP-stalk-HC Fusion protein

<400> SEQUENCE: 11

Tyr Phe Pro Ser Tyr Ile
1               5

<210> SEQ ID NO 12
<211> LENGTH: 7
<212> TYPE: PRT
<213> ORGANISM: Artificial Sequence
<220> FEATURE:
<223> OTHER INFORMATION: a RFP-stalk and RFP-stalk-HC Fusion protein

<400> SEQUENCE: 12

Tyr Phe Pro Ser Tyr Ile Phe
1 5

<210> SEQ ID NO 13
<211> LENGTH: 8
<212> TYPE: PRT
<213> ORGANISM: Artificial Sequence
<220> FEATURE:
<223> OTHER INFORMATION: a RFP-stalk and RFP-stalk-HC Fusion protein

<400> SEQUENCE: 13

Tyr Phe Pro Ser Tyr Ile Phe Leu
1 5

<210> SEQ ID NO 14
<211> LENGTH: 9
<212> TYPE: PRT
<213> ORGANISM: Artificial Sequence
<220> FEATURE:
<223> OTHER INFORMATION: a RFP-stalk and RFP-stalk-HC Fusion protein

<400> SEQUENCE: 14

Tyr Phe Pro Ser Tyr Ile Phe Leu His
1 5

<210> SEQ ID NO 15
<211> LENGTH: 10
<212> TYPE: PRT
<213> ORGANISM: Artificial Sequence
<220> FEATURE:

<223> OTHER INFORMATION: a RFP-stalk and RFP-stalk-HC Fusion protein

<400> SEQUENCE: 15

Tyr Phe Pro Ser Tyr Ile Phe Leu His Leu
1               5                   10

<210> SEQ ID NO 16
<211> LENGTH: 15
<212> TYPE: PRT
<213> ORGANISM: Artificial Sequence
<220> FEATURE:
<223> OTHER INFORMATION: a RFP-stalk and RFP-stalk-HC Fusion protein

<400> SEQUENCE: 16

Tyr Phe Pro Ser Tyr Ile Phe Leu His Leu Val His Gly Leu Ala
1               5                   10                  15

<210> SEQ ID NO 17
<211> LENGTH: 20
<212> TYPE: PRT
<213> ORGANISM: Artificial Sequence
<220> FEATURE:
<223> OTHER INFORMATION: a RFP-stalk and RFP-stalk-HC Fusion protein

<400> SEQUENCE: 17

Tyr Phe Pro Ser Tyr Ile Phe Leu His Leu Val His Gly Leu Ala Ala
1               5                   10                  15

Val Pro Leu Val
            20

<210> SEQ ID NO 18
<211> LENGTH: 25
<212> TYPE: PRT
<213> ORGANISM: Artificial Sequence
<220> FEATURE:
<223> OTHER INFORMATION: a RFP-stalk and RFP-stalk-HC Fusion protein

<400> SEQUENCE: 18

Tyr Phe Pro Ser Tyr Ile Phe Leu His Leu Val His Gly Leu Ala Ala
1               5                   10                  15

Val Pro Leu Val Tyr Leu Ile Cys His
            20                  25

<210> SEQ ID NO 19
<211> LENGTH: 30
<212> TYPE: PRT
<213> ORGANISM: Artificial Sequence
<220> FEATURE:
<223> OTHER INFORMATION: a RFP-stalk and RFP-stalk-HC Fusion protein

<400> SEQUENCE: 19

Tyr Phe Pro Ser Tyr Ile Phe Leu His Leu Val His Gly Leu Ala Ala
1               5                   10                  15

Val Pro Leu Val Tyr Leu Ile Cys His Ala Ser Gln Leu Leu
            20                  25                  30